US010426893B2

(12) United States Patent
Marsh et al.

(10) Patent No.: US 10,426,893 B2
(45) Date of Patent: Oct. 1, 2019

(54) DRUG DELIVERY DEVICE WITH THREADED HOUSING AND PISTON, AND METHOD FOR MANUFACTURING THE SAME

(71) Applicant: Sanofi, Paris (FR)

(72) Inventors: William Marsh, Buckinghamshire (GB); Anthony Paul Morris, Coventry (GB)

(73) Assignee: Sanofi, Paris (FR)

( * ) Notice: Subject to any disclaimer, the term of this patent is extended or adjusted under 35 U.S.C. 154(b) by 412 days.

(21) Appl. No.: 15/321,998

(22) PCT Filed: Jul. 1, 2015

(86) PCT No.: PCT/EP2015/064966
§ 371 (c)(1),
(2) Date: Dec. 23, 2016

(87) PCT Pub. No.: WO2016/001292
PCT Pub. Date: Jan. 7, 2016

(65) Prior Publication Data
US 2017/0157330 A1    Jun. 8, 2017

(30) Foreign Application Priority Data

Jul. 1, 2014   (EP) ..................... 14306061

(51) Int. Cl.
*A61M 5/315*   (2006.01)
*A61M 5/31*    (2006.01)
(Continued)

(52) U.S. Cl.
CPC .......... *A61M 5/31553* (2013.01); *A61M 5/20* (2013.01); *A61M 5/31515* (2013.01);
(Continued)

(58) Field of Classification Search
CPC ................ A61M 5/31553; A61M 5/20; A61M 5/31515; A61M 5/31541; A61M 5/31583; A61M 5/31585
See application file for complete search history.

(56) References Cited

U.S. PATENT DOCUMENTS

2008/0051712 A1* 2/2008 Fiechter ............ A61M 5/31553
604/134

FOREIGN PATENT DOCUMENTS

WO        2891071       11/1972
WO     WO 99/38554      8/1999
(Continued)

OTHER PUBLICATIONS

International Search Report and Written Opinion in International Application No. PCT/EP2015/064966, dated Sep. 8, 2015, 13 pages.

(Continued)

*Primary Examiner* — Edelmira Bosques
(74) *Attorney, Agent, or Firm* — Fish & Richardson P.C.

(57) ABSTRACT

A drug delivery device for selecting and dispensing a number of user variable doses of a medicament includes a housing having a tubular portion with an inner thread, a piston rod having a threaded portion and a distal end, and a bearing having a distal face and a proximal face. The bearing includes a retaining stem protruding from the proximal face. The piston rod includes a distal portion having an outer diameter which is smaller than the inner diameter of the inner thread of the tubular portion and comprising at its distal end at least one retaining clip engaging the retaining stem. The axial length of the tubular portion is smaller than or equal to the axial distance between the proximal face of the bearing disc and the distal end of the threaded portion of the piston rod. During manufacturing of the device, the retaining clip engages the retaining stem prior to the inner (Continued)

thread of the tubular portion engages with the threaded portion of the piston rod.

13 Claims, 8 Drawing Sheets

(51) Int. Cl.
  *B29C 45/26* (2006.01)
  *A61M 5/20* (2006.01)
  *B29C 45/44* (2006.01)

(52) U.S. Cl.
  CPC .... *A61M 5/31541* (2013.01); *A61M 5/31561* (2013.01); *A61M 5/31583* (2013.01); *A61M 5/31585* (2013.01); *B29C 45/2618* (2013.01); *A61M 2005/202* (2013.01); *A61M 2005/3126* (2013.01); *A61M 2005/3154* (2013.01); *A61M 2005/31523* (2013.01); *A61M 2205/581* (2013.01); *A61M 2205/582* (2013.01); *A61M 2205/583* (2013.01); *A61M 2207/00* (2013.01); *B29C 45/44* (2013.01)

(56) References Cited

FOREIGN PATENT DOCUMENTS

| | | |
|---|---|---|
| WO | WO 2008/063529 | 5/2008 |
| WO | WO 2009/132781 | 11/2009 |
| WO | WO 2010/139641 | 12/2010 |
| WO | WO 2011/039226 | 4/2011 |
| WO | WO 2011/039229 | 4/2011 |
| WO | WO 2011/060785 | 5/2011 |
| WO | WO 2012/062718 | 5/2012 |

OTHER PUBLICATIONS

International Preliminary Report on Patentability in International Application No. PCT/EP2015/064966, dated Jan. 3, 2017, 9 pages.

* cited by examiner

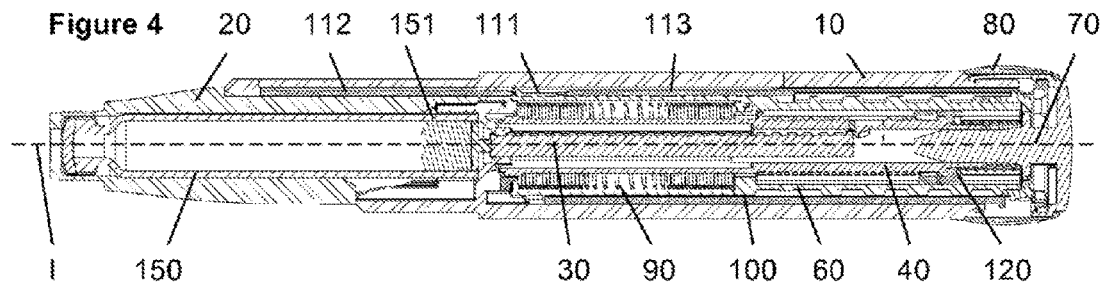
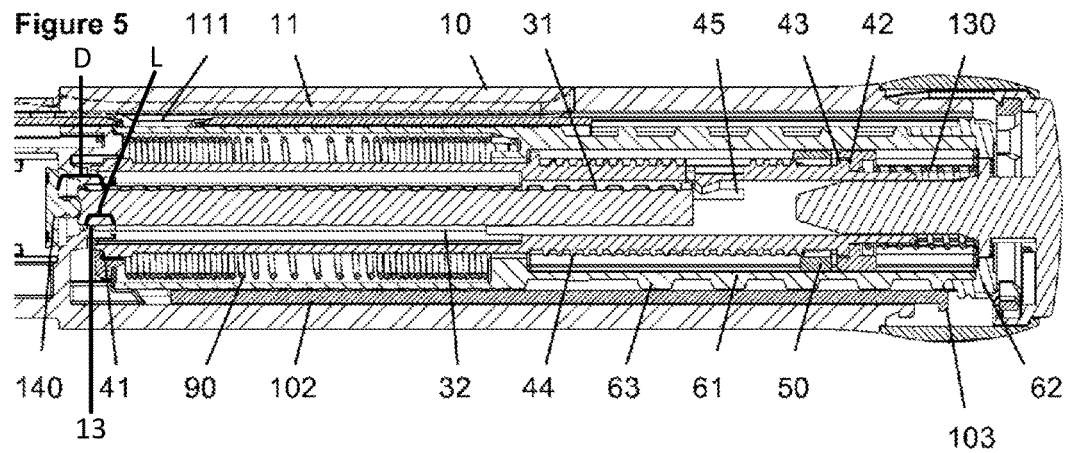
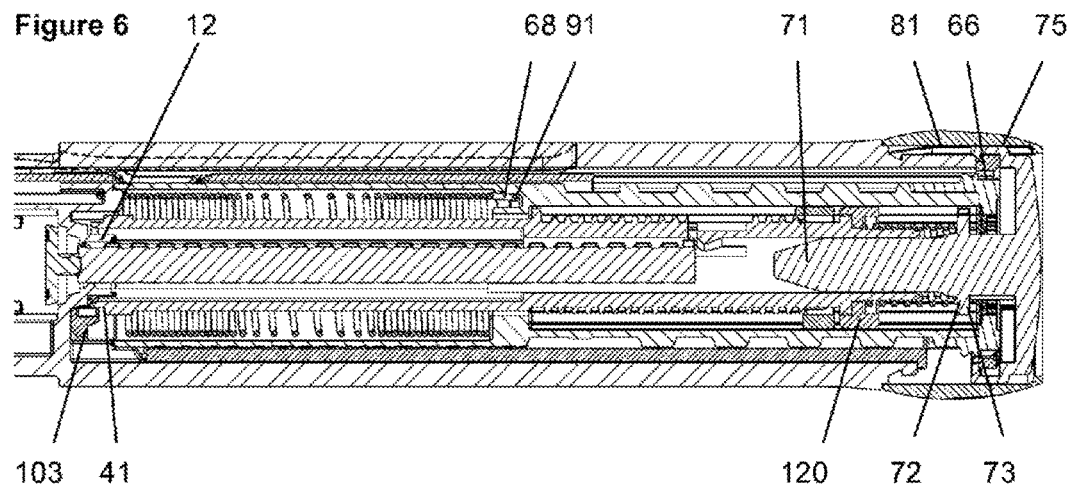

DRUG DELIVERY DEVICE WITH THREADED HOUSING AND PISTON, AND METHOD FOR MANUFACTURING THE SAME

CROSS-REFERENCE TO RELATED APPLICATIONS

This application is a U.S. national stage application under 35 USC § 371 of International Application No. PCT/EP2015/064966, filed on Jul. 1, 2015, which claims priority to European Patent Application No. 14306061.4 filed on Jul. 1, 2014, the entire contents of which are incorporated herein by reference.

TECHNICAL FIELD

The present disclosure is generally directed to a drug delivery device for selecting and dispensing a number of user variable doses of a medicament and to a method for manufacturing such a device.

BACKGROUND

Pen type drug delivery devices have application where regular injection by persons without formal medical training occurs. This may be increasingly common among patients having diabetes where self-treatment enables such patients to conduct effective management of their disease. In practice, such a drug delivery device allows a user to individually select and dispense a number of user variable doses of a medicament.

There are basically two types of drug delivery devices: resettable devices (i.e., reusable) and non-resettable (i.e., disposable). For example, disposable pen delivery devices are supplied as self-contained devices. Such self-contained devices do not have removable pre-filled cartridges. Rather, the pre-filled cartridges may not be removed and replaced from these devices without destroying the device itself. Consequently, such disposable devices need not have a resettable dose setting mechanism.

A further differentiation of drug delivery device types refers to the drive mechanism: There are devices which are manually driven, e.g. by a user applying a force to an injection button, devices which are driven by a spring or the like and devices which combine these two concepts, i.e. spring assisted devices which still require a user to exert an injection force. The spring-type devices involve springs which are preloaded and springs which are loaded by the user during dose selecting. Some stored-energy devices use a combination of spring preload and additional energy provided by the user, for example during dose setting.

These types of pen delivery devices (so named because they often resemble an enlarged fountain pen) generally comprise three primary elements: a body cartridge section that includes a cartridge often contained within a housing or holder; a needle assembly connected to one end of the cartridge section; and a dosing section connected to the other end of the cartridge section. A cartridge (often referred to as an ampoule) typically includes a reservoir that is filled with a medication (e.g., insulin), a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

The needle assembly is typically a replaceable double-ended needle assembly. Before an injection, a replaceable double-ended needle assembly is attached to one end of the cartridge assembly, a dose is set, and then the set dose is administered. Such removable needle assemblies may be threaded onto, or pushed (i.e., snapped) onto the pierceable seal end of the cartridge assembly.

The dosing section or dose setting mechanism is typically the portion of the pen device that is used to set (select) a dose. During an injection, a spindle or piston rod contained within the dose setting mechanism presses against the bung or stopper of the cartridge. This force causes the medication contained within the cartridge to be injected through an attached needle assembly. After an injection, as generally recommended by most drug delivery device and/or needle assembly manufacturers and suppliers, the needle assembly is removed and discarded.

Typically, an injection device comprises a lead screw or piston rod, which is driven by a drive member during dose dispensing to act on a cartridge bung. If the lead screw rotates during dose dispensing, friction occurs with respect to the (rotationally static) cartridge bung. A bearing may be provided to minimize friction.

In a very simple form, a drug delivery device comprises a housing defining a longitudinal axis and having a tubular portion with an inner thread, a piston rod having a threaded portion with a distal end, and a bearing disc having a distal face and a proximal face. For example, the piston rod may be used for selecting and dispensing a number of user variable doses of a medicament from a reservoir in the housing or a cartridge.

WO 2010/139641 A1 discloses a spindle and bearing combination for use in a more complex drug delivery device comprising a rotatable spindle having a distal end and a disk-shaped bearing attached to the distal end of the spindle through a first connection comprising a web that fixedly attaches the bearing to the spindle to prevent independent movement of the bearing relative to the spindle. This first connection is replaced by a second connection which is created when the web is severed and the web is disconnected from the bearing.

Further, WO 2009/132781 A1 discloses a dosing mechanism which includes a piston rod of generally circular cross-section. A pressure foot is located at the distal end of the piston rod. The pressure foot is made of two separate parts which are snapped together around a distal end portion of the piston rod. The pressure foot is disposed to abut the proximal face of a piston.

Assembly of known drug delivery devices with a threaded housing part and a threaded piston rod typically requires relative rotation of the housing part and the piston rod. A rotational assembly movement is more complicated than a mere axial movement. Further, attachment of the pressure foot or bearing disc includes in some cases complex steps.

SUMMARY

Certain embodiments are not directed to so called fixed dose devices which only allow dispensing of a predefined dose without the possibility to increase or decrease the set dose. Certain embodiments are applicable for both disposable devices as well as for reusable devices. Certain embodiments provide drug delivery devices facilitating assembly.

According to a first embodiment the drug delivery device comprises a housing defining a longitudinal axis and having a tubular portion with an inner thread, a piston rod having a threaded portion with a distal end, and a bearing disc having a distal face and a proximal face.

The bearing disc comprises a retaining stem protruding from the proximal face and the piston rod comprises a distal portion having an outer diameter which is smaller than the inner diameter of the inner thread of the tubular portion and comprising at its distal end at least one retaining clip engaging the retaining stem. For example, the bearing is axially clipped or snapped to the threaded piston rod, but is free to rotate relative thereto. If the axial length of the tubular portion is smaller than or equal to the axial distance between the proximal face of the bearing disc and the distal end of the threaded portion of the piston rod, assembly of the device may simply require an axial relative movement of the piston rod relative to the bearing disc. In other words, the snap engagement of the retaining clip receiving the retaining stem may occur prior to the threads of the tubular housing portion and the piston rod engaging. Thus, no rotation of the piston rod relative to the housing is required. Rather, the piston rod thread may engage the housing thread only at a later stage during assembly, during priming of the device or even during the first use of the device by a patient. Preferably, the length of the tubular portion and the axial distance between the proximal face of the bearing disc and the distal end of the threaded portion of the piston rod are chosen such that the most distal thread pitch of the piston rod axially abuts without meshing the most proximal thread pitch of the tubular housing portion upon engagement of the retaining stem and the retaining clip. For example, the axial length of the tubular portion may be smaller than or equal to the axial length of the distal portion of the piston rod.

The housing with its tubular threaded portion may be a single component or alternatively a multi-component part, e.g. comprising an outer housing shell and a threaded insert which is axially and/or rotationally fixed within the outer housing shell. The tubular threaded housing portion may be provided on a radially inwards facing wall or web.

Insertion of the piston rod into the housing is further facilitated if the distal portion of the piston rod has, at least in regions, a cylindrical outer surface. Thus, the distal portion of the piston rod may slide without interference through the threaded housing portion until the piston rod engages the bearing disc. Preferably, the distal portion of the piston rod mainly (or even only) consists of distally extending snap arms for engaging the retaining stem.

In a preferred embodiment, the internal faces of the retaining clip subtend a total angle between 150° and 190°, preferably between 170° and 185°, about the longitudinal axis of the piston rod. This allows manufacturing the piston rod using a simple open and shut moulding, for example using only two tool parts that slide relative to each other along the same axis. If the internal faces of the clip on the threaded rod subtend a total angle of not significantly more than 180° about a longitudinal axis, the tool does not interfere with the moulded part during opening.

According to an embodiment, none of the clip feature surfaces of the threaded piston rod are hidden when viewed from either one or the other of two directions. Preferably, the surface of the threaded piston rod is completely visible from either one or the other of two directions. In other words, the surface of the threaded piston rod can preferably be projected onto two parallel planes without overlap of the projected surfaces.

To reduce friction, a first convex contact surface may be provided on one of the retaining stem and the retaining clip and a second, preferably concave, contact surface may be provided on the other of the retaining stem and the retaining clip, wherein the radius of curvature of the first convex contact surface is smaller than the radius of curvature of the second contact surface. This results in a point contact between the bearing and the threaded rod, although contact pressure at the interface may deform the materials and cause contact over a small and approximately circular area. The curvature of the convex contact surface and the concave contact surface are chosen such that the contact diameter between the bearing and the threaded rod is small to minimize the frictional losses at this interface. Other arrangements would have the same effect, e.g. a small flat surface on one part contacting a larger flat on the other, or a convex surface on one part contacting a flat surface on the other.

The bearing comprises a disc and a stem, which extends in a proximal direction from the disc. At least one clip arm may be located at the distal end of the threaded piston rod defining an insertion space for receiving the stem. Preferably, two clip arms are provided equally spaced and distributed about the central axis of the rod. The concave contact surface may be located between the clip arms and off-set in the proximal direction with respect to the distal end of the clip arms. The at least one clip arm may have retention features for snap-engaging a corresponding feature on the retaining stem of the bearing.

To facilitate assembly of the piston rod through a threaded element of an injection device, the threaded rod may have an outer thread with a flute base having a first diameter and the at least one clip arm may have an at least partially cylindrical outer surface with a second diameter with the first diameter being equal to or less than the second diameter. In addition, the thread of the threaded rod may have a large lead-in to engage easily with a corresponding thread e.g. of the housing. This enlarged lead-in may have the form of a wedge-shaped introduction section.

In a preferred embodiment the interface comprises a stem of the bearing having the convex contact surface at its proximal end and further comprising a recessed portion located on the stem distally with respect to the convex contact surface. The recessed portion allows snap-engagement with the threaded rod. This design of the bearing and the leadscrew can be manufactured with low effort using open and shut mould tooling.

In a device requiring rotation of the piston rod during dose dispensing, torque has to be transmitted into the piston rod. For this purpose, the threaded piston rod may have an axially extending groove or spline. In other words, the piston rod may be rotationally constrained to a further component, such as a driver tube, while being axially displaceable with respect to such a driver.

In some aspects, an injection device may comprise the piston rod as mentioned above and in addition a dose setting member rotatable relative to the housing during dose setting, a drive member which is rotationally constrained to the housing, for example via a locking arm, in a first dose setting mode and which is rotatable relative to the housing in a second dose dispensing mode, a locking element which is permanently rotationally constrained to the housing and movable relative to the housing in a direction parallel to the longitudinal axis between a first dose setting position and a second dose dispensing position, an actuation button movable relative to the housing in a direction parallel to the longitudinal axis between a first dose setting position and a second dose dispensing position for switching the injection device between the first dose setting mode and the second dose dispensing mode, a ratchet for transmitting torque from the dose setting member to the drive member during dose dispensing and allowing relative rotational movement between the dose setting member and the drive member during dose setting, the ratchet comprising first ratchet features rotationally constrained to the driver and second ratchet features rotationally constrained to the dose setting member, and a spring. The spring may bias the locking element and the actuation button into their first dose setting position and in addition biasing the first ratchet features into engagement with the second ratchet features. Thus, one single spring, preferably a compression spring, is sufficient for biasing the actuation button and the locking element into the dose setting position or mode. As an ancillary effect, the same spring may be used to keep two ratchet elements into engaging contact, which facilitates dose setting and dose dispensing. In other words, an additional compression spring required in known devices can be omitted which does not only reduce the costs for the components of the device but also reduces the time and effort required during assembly of the device.

In an alternative embodiment, the drive member may be axially movable within the housing for rotationally engaging or disengaging the drive member and the housing. In other words, the locking arm may be omitted with the drive member being axially movable between a dose setting position and a dose dispensing position. Preferably, in this alternative embodiment the spring is located interposed between the drive member and the housing such that the drive member is biases into its, e.g. proximal, dose setting position relative to the housing.

Preferably, the actuation button is axially constrained and rotatable relative to the locking element or the drive member. For example, the actuation button may be snapped or clipped onto the locking element. This axial constraint results in the actuation button and the locking element behaving as one single component regarding their axial movements. An advantage of this design may be seen in avoiding possible clearances between the actuation button and the locking element. The actuation button is preferably provided with a central stem extending from a proximal actuation area. A bead or flange may be provided on this stem with the compression spring abutting this bead or flange. As an alternative, the compression spring may be arranged such that it acts on the locking element which in turn entrains the actuation button.

Preferably, the locking element comprises an arm portion extending parallel to the longitudinal axis between the housing and the drive member. The first clutch may be provided at one end of the arm portion and the actuation button may be attached to the opposite end of the arm portion.

The ratchet permits the dose setting member to rotate during dose setting without affecting the driver, but ensures that the driver is moved together with the dose setting member during dose dispensing. In addition to dose setting and dose dispensing it may be required to correct a dose, i.e. to decrease the set dose. Preferably, the first ratchet features and the second ratchet features comprise teeth having a ramp angles allowing to overhaul the ratchet for dose correction. During dose setting and during dose correction, the teeth of the ratchet features bump over each other against the force of the spring biasing these teeth into engagement. Thus, the ratchet allows relative rotational movement between the dose setting member and the drive member in two opposite directions during dose setting and dose correction.

For an injection device using a torsion spring or the like for generating the force or torque required for dose dispensing, the ratchet typically has to withstand this torque or force, which is a function of the axial load applied by the spring, the ramp angle of the ratchet, the friction coefficient between the mating surfaces and the mean radius of the ratchet features and the torque applied by the torsion spring. It may be desirable to choose different ramp angles for clockwise and anti-clockwise relative rotation of the ratchet features during dose setting and dose dispensing to compensate the effect of the torsion spring such that the force or torque required to overhaul the ratchet is similar for dose setting and dose correction.

According to a preferred embodiment the housing has a first aperture or window, a dose indicator positioned within the housing and rotatable with respect to the housing during dose setting and during dose dispensing, and a gauge element, which is interposed between the housing and the dose indicator. The gauge element has a second aperture or window, which is positioned with respect to the first aperture or window of the housing such that at least a part of the dose indicator is visible through the first and second apertures or windows. Further, the gauge element is axially guided within the housing and in threaded engagement with the dose indicator such that rotation of the dose indicator causes an axial displacement of the gauge element. The injection device further comprises a resilient member adapted to provide a force necessary for ejecting a dose from the injection device.

The position of the gauge element may thus be used to identify the actually set and/or dispensed dose. Different colours of sections of the gauge member may facilitate identifying the set and/or dispensed dose without reading numbers, symbols or the like on a display. As the gauge element is in threaded engagement with the dose indicator, rotation of the dose indicator causes an axial displacement of the gauge element relative to the dose indicator and relative to the housing. The gauge element may have the form of a shield or strip extending in the longitudinal direction of the device. As an alternative, the gauge element may be a sleeve. In an embodiment, the dose indicator is marked with a sequence of numbers or symbols and the gauge element comprises an aperture or window. With the dose indicator located radially inwards of the gauge element, this allows that at least one of the numbers or symbols on the dose indicator is visible through the aperture or window. In other words, the gauge element may be used to shield or cover a portion of the dose indicator and to allow view only on a limited portion of the dose indicator. This function may be in addition to the gauge element itself being suitable for identifying or indicating the actually set and/or dispensed dose.

Providing a resilient member, such as a spring, generating the force or torque required for dose dispensing reduces the user applied forces for dose dispensing. This is especially helpful for users with impaired dexterity. In addition, the dial extension of the known manually driven devices, which is a result of the required dispensing stroke, may be omitted by providing the resilient member because merely a small triggering stroke may be necessary for releasing the resilient member.

In general, the concept of the gauge element and the dose indicator is applicable for various types of devices with or without a drive spring. In the preferred embodiment, the resilient member may be a spring which is preloaded or a spring which is loaded by the user during dose selecting. This includes devices which use a combination of spring preload and additional energy provided by the user, for example during dose setting. Preferably, the resilient member may be a torsion spring which is preferably strained during dose setting. The torsion spring may have one end attached to the housing and the other end attached to the dose indicator. As an alternative, the resilient member may comprise a reverse wound flat spiral spring as a power reservoir having a first end attached to a first spool and a second end attached to a second spool, which is axially and rotationally constrained to a drive member, which is for example rotationally constrained to a piston rod.

The attachment of e.g. a torsion spring to e.g. the dose indicator has to be durable and reliable to prevent uncoupling of the spring. Taking into account efficiency during assembly of an injection device, it is required to constrain the spring with a minimum effort. One way to achieve this, may be providing an anchor point or a pocket in the dose indicator or the like component and providing a hook at the end of the spring which is to be attached to the e.g. dose indicator. If a preload is exerted on the spring, the hook may be biased into engagement with the anchor point, helping to prevent disassembly during subsequent assembly steps. In addition or as an alternative, a groove may be provided in the e.g. dose indicator for receiving at least a part of the first spring coil, wherein the groove has an end feature that is in interference with the end of the spring. For example, a ramp may be provided at the end of a groove which ramp deflects a spring hook or the like spring end in a radial direction, e.g. radially inwards, generating a force in the spring, causing a contact force between the ramp and the spring end, and anchoring the spring due to frictional forces. A flange may be provided for reinforcement of this connection area of the dose indicator or the like.

In a preferred embodiment, the dose indicator, during dose setting, is adapted to undergo a mere rotational movement within the housing and relative to the housing. In other words, the dose indicator does not perform a translational movement during dose setting. This prevents that the dose indicator is wound out of the housing or that the housing has to be prolonged for covering the dose indicator within the housing.

It is preferred if the device is suitable for dispensing variable, user-selectable, doses of medicament. The device may be a disposable device, i.e. a device which does not provide for an exchange of an empty cartridge.

According to a preferred embodiment, the drug delivery device comprises a limiter mechanism defining a maximum settable dose and a minimum settable dose. Typically, the minimum settable dose is zero (0 IU of insulin formulation), such that the limiter stops the device at the end of dose dispensing. The maximum settable dose, for example 60, 80 or 120 IU of insulin formulation, may be limited to reduce the risk of overdosage and to avoid the additional spring torque needed for dispensing very high doses, while still being suitable for a wide range of patients needing different dose sizes. Preferably, the limits for the minimum dose and the maximum dose are provided by hard stop features. The limiter mechanism may comprise a first rotational stop on the dose indicator and a first counter stop on the gauge element, which abut in the minimum dose (zero) position, and a second rotational stop on the dose indicator and a second counter stop on the gauge element, which abut in the maximum dose position. As the dose indicator rotates relative to the gauge element during dose setting and during dose dispensing, these two components are suitable to form a reliable and robust limiter mechanism.

The drug delivery device may comprise a last dose protection mechanism for preventing the setting of a dose, which exceeds the amount of liquid left in a cartridge. This has the advantage that the user knows how much will be delivered before starting the dose delivery. It also ensures that dose delivery stops in a controlled manner without the bung entering the neck portion of the cartridge where the diameter is smaller which may result in an underdose. In a preferred embodiment, this last dose protection mechanism only detects the medicament remaining in the cartridge when the cartridge contains less than the maximum dose (e.g. 120 IU). For example, the last dose protection mechanism comprises a nut member interposed between the drive member and a component which rotates during dose setting and dose dispensing. The component which rotates during dose setting and dose dispensing may be the dose indicator or a dial sleeve rotationally constrained to the dose indicator. In a preferred embodiment, the dose indicator and/or a dial sleeve rotate during dose setting and during dose dispensing, whereas the drive member only rotates during dose dispensing together with the dose indicator and/or the dial sleeve. Thus, in this embodiment, the nut member will only move axially during dose setting and will remain stationary with respect to these components during dose dispensing. Preferably, the nut member is threaded to the drive member and splined to the dose indicator and/or the dial sleeve. As an alternative, the nut member may be threaded to the dose indicator and/or the dial sleeve and may be splined to the drive member. The nut member may be a full nut or a part thereof, e.g. a half nut.

The injection device may comprise at least one clicker mechanism for generating a tactile and/or audible feedback. During dose setting re-engagement of the ratchet teeth (between the driver and a clutch plate, dose indicator or dose setting member) may generate an audible and/or tactile feedback. For example, a tactile feedback during dose dispense may be provided via a compliant cantilever clicker arm integrated into the proximal end of the locking element. This clicker arm may interface radially with ratchet features (e.g. a ring of teeth) provided on the outer surface of the proximal end of the dose indicator, whereby the ratchet tooth spacing corresponds to the dose indicator rotation required for a single increment dispense. During dispense, as the dose indicator rotates and the locking element is rotationally coupled to the housing, the ratchet features engage with the clicker arm to produce an audible click with each dose increment delivered.

In addition or as an alternative to this feedback during dose dispense, the clicker mechanism signifies the end of dose dispensing. At the end of dose, an audible feedback may be provided in the form of a "click", distinct from the "clicks" provided during dispense, to inform the user that the device has returned to its zero position. In a preferred embodiment this feedback is generated by the interaction of three components, the dose indicator, gauge element and locking element with a pivotable clicker arm arranged via a torsion beam on the locking element which arm and ratchet features (e.g. a ring of teeth) provided on the outer surface of the dose indicator. The movement of the locking element between its first dose setting position and its second dose dispensing position, together with the movement of the gauge element back towards its zero dose position, may be used to pivot the clicker arm from a non-deflected position during dose setting into a position engaging the ratchet features on the dose indicator during dose dispensing. This embodiment allows feedback to only be created at the end of dose delivery and not created if the device is dialled back to, or away from, the zero position.

In a preferred embodiment, the device comprises at least a first clicker producing an audible and/or tactile first feedback during dose setting and/or dose dispensing and a second clicker producing an audible and/or tactile second feedback, distinct from the first feedback, during dose dispensing when the device reaches its minimum dose (zero) position. The injection device may have different clickers active during dose setting and during dose dispensing.

Spring loaded injection devices often comprise an actuation element for releasing the energy stored in the resilient member, e.g. in the spring. Typically, the user presses or activates this actuating element after a dose has been set to initiate dose dispensing. According to a preferred embodiment, the actuating element is the actuation button for switching the injection device between the first dose setting mode and the second dose dispensing mode. The actuation button may be located at the proximal end of the housing, i.e. the end facing away from the needle.

The injection device may further comprise a second clutch rotationally coupling the actuation button to the dose indicator when the actuation button and the locking element are in the first dose setting position and de-coupling the actuation button from the dose indicator when the actuation button and the locking element are in the second dose dispensing position. Thus, the actuation button entrains the dose indicator during dose setting, but allows the actuation button to stand still as the dose indicator rotates during dose dispensing.

The drug delivery device may comprise a cartridge containing a medicament. The term "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(02)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

A method for manufacturing a drug delivery device may comprise the steps of providing the housing, the piston rod and the bearing disc, inserting the bearing disc from the distal end into the housing such that the retaining stem extends into the tubular portion and inserting the piston rod from the proximal end into the housing such that the retaining clip engages the retaining stem, wherein the retaining clip engages the retaining stem prior to the inner thread of the tubular portion engages with the threaded portion of the piston rod. Preferably, the bearing disc is introduced into the housing prior to insertion of the piston rod into the housing. This may have an advantage when several component parts are to be inserted from the proximal side of the housing after attachment of the piston rod with the bearing disc. As an alternative, the piston rod may be introduced into the housing prior to the bearing disc.

Preferably, the piston rod is inserted into the housing by an axial movement parallel to the longitudinal axis of the housing without a rotational movement. This facilitates assembly.

In a further preferred embodiment, the piston rod is open and shut moulded using only two tool parts that slide relative to each other along the same axis.

BRIEF DESCRIPTION OF THE DRAWINGS

Non-limiting, exemplary embodiments will now be described with reference to the accompanying drawings, in which:

FIG. 4 shows a sectional view of the device of FIG. 1;

FIG. 5 shows an enlarged view of a detail of the device of FIG. 1 in the dose setting mode;

FIG. 6 shows the enlarged view of a detail of FIG. 5 in the dose dispensing mode;

DETAILED DESCRIPTION

Figure 1:
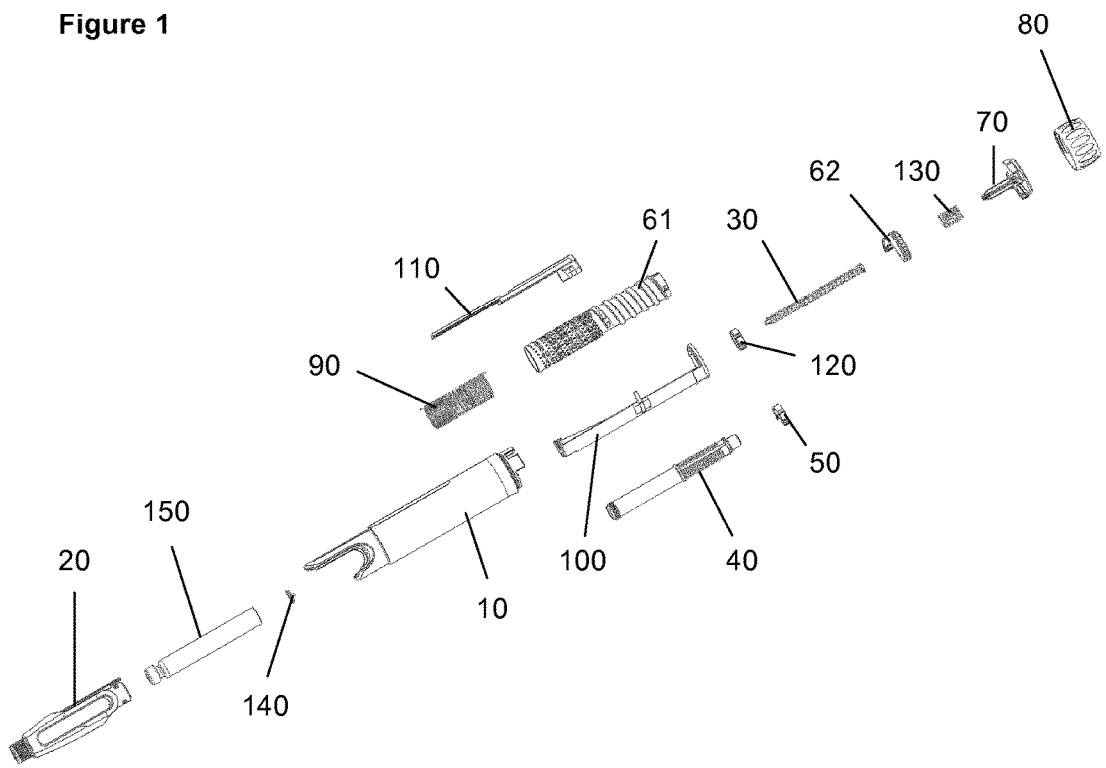
FIG. 1 shows an exploded view of the components of an injection device.
Figure 2:
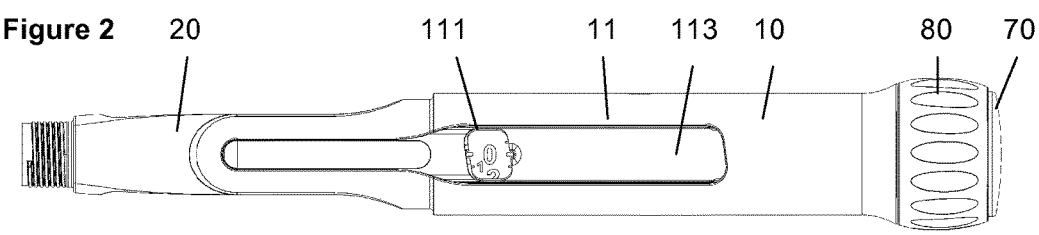
FIG. 2 shows a top view of the device of FIG. 1 in the minimum dose position.

FIG. 2 shows a drug delivery device in the form of an injection pen. The device has a distal end (left end in FIG. 2) and a proximal end (right end in FIG. 2). The component parts of the drug delivery device are shown in FIG. 1. The drug delivery device comprises a housing 10, a cartridge holder 20, a lead screw (piston rod) 30, a driver 40, a nut 50, a dose indicator (number sleeve) 60, a button 70, a dose selector 80, a torsion spring 90, a locking arm 100, a gauge element 110, a clutch plate 120, a clutch spring 130, a bearing 140 and a cartridge 150. A needle arrangement (not shown) with a needle hub and a needle cover may be provided as additional components, which can be exchanged as explained above. A longitudinal axis I of the device is shown in FIG. 4.

The housing 10 or body is a generally tubular element. In the embodiment shown in the figures, the housing 10 provides location for the liquid medication cartridge 150 and cartridge holder 20, an interface to prevent rotation of the locking arm 100 and the gauge element 110, a slot 11 or lens through which the dose number on the dose indicator 60 can be viewed, and a feature, e.g. a circumferential groove, on its external surface to axially retain the dose selector 80. A flange-like or cylindrical inner wall 12 comprises an inner thread 13 engaging the piston rod 30. An axial length L of the flange-like or cylindrical inner wall 12 is smaller than or equal to an axial distance D between the proximal face of the bearing 140 and the distal end of the outer thread 31 of the lead screw 30 (FIG. 5).

The cartridge holder 20 is located at the distal side of housing 10 and permanently attached thereto. The cartridge holder may be a transparent or translucent component which is tubular to receive cartridge 150. The distal end of cartridge holder 20 may be provided with means for attaching a needle arrangement. A removable cap (not shown) may be provided to fit over the cartridge holder 20 and may be retained via clip features.

The lead screw 30 is an elongate member with an outer thread 31 (FIG. 16) which is rotationally constrained to the driver 40 via a splined interface. The thread 31 may have a large lead-in, for example a wedge shape form, at its distal end to engage a corresponding housing thread form on the first rotation. The interface comprises at least one longitudinal groove or track 32 (FIG. 17) and a corresponding protrusion or spline of the driver 40. When rotated, the lead screw 30 is forced to move axially relative to the driver 40, through its threaded interface with the housing 10. At its distal end, the lead screw 30 is provided with an interface for clip attachment of the bearing 140. In the present embodiment, this interface comprises two clip arms 33 extending in the distal direction defining an insertion space between them for insertion of a bearing 140 interface. As an alternative, the interface may comprise only one single clip arm extending more than 180° about the longitudinal axis, or may comprise one or several clip arms 33. The clip arm(s) 33 may have a bended form with a recessed clip portion as shown in FIG. 17. Preferably, the clip arm(s) form a cylindrical outer face having a diameter equal to or smaller than the outer diameter of the lead screw 30 at the ground of the groove (flute base) of the outer thread 31. A concave contact surface 34 is provided between the clip arms 33 for abutment of a corresponding portion of bearing 140.

Figure 11:
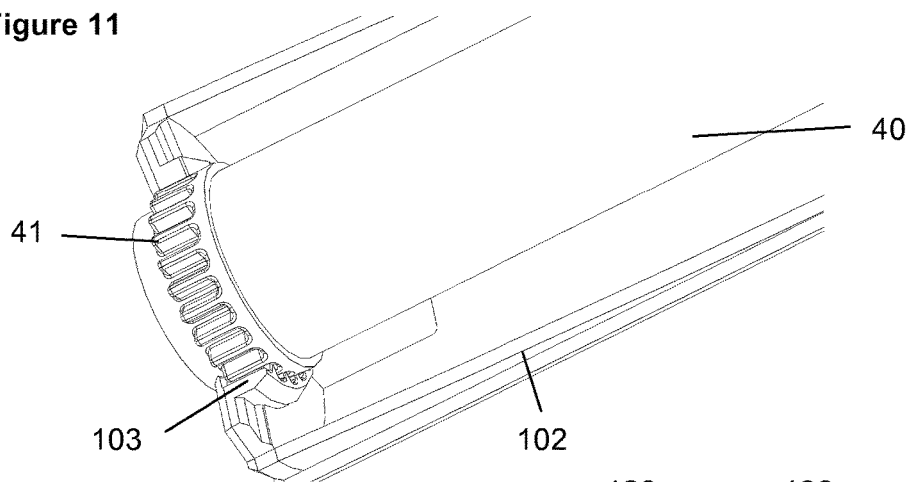
FIG. 11 shows an enlarged detail of the driver of the device of FIG. 1.
Figure 12:
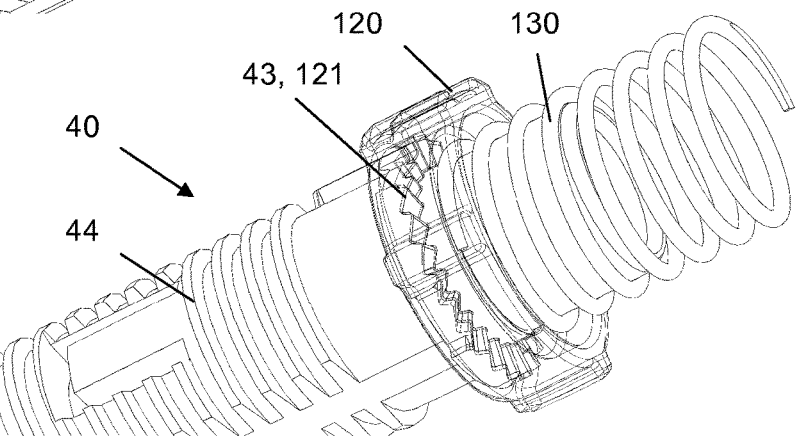
FIG. 12 shows an enlarged detail of the driver, the clutch plate and the clutch spring of the device of FIG. 1.
Figure 13:
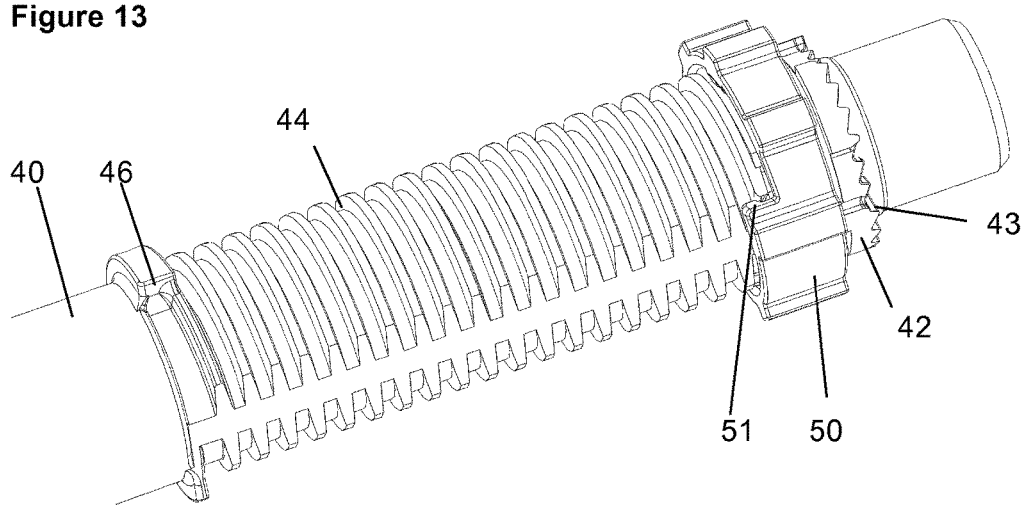
FIG. 13 shows an enlarged detail of the driver and the nut of the device of FIG. 1.

The driver 40 is a sleeve which extends from the interface with the dose indicator (number sleeve) 60 via the clutch plate 120 down to a splined tooth interface 41 (FIG. 11) with the locking arm 100. This provides rotational constraint of the locking arm 100 to the driver 40 during dose setting. When the button 70 is pressed, these spline teeth are disengaged allowing the driver 40 to rotate. Further, teeth 42 are provided near the proximal end on a flange 43 of driver 40 for engagement with clutch plate 120 (FIG. 12). The driver 40 has a threaded section 44 providing a helical track for the nut 50 (FIG. 13). In addition, a last dose abutment or stop 46 is provided which may be the end of the thread 44 track or preferably a rotational hard stop for interaction with a corresponding last dose stop 51 of nut 50, thus limiting movement of the nut 50 on the thread 44. At least one longitudinal spline 45 engages a corresponding track 32 of the lead screw 30.

The nut 50 is part of a last dose limiter mechanism. The nut 50 is located between the dose indicator (number sleeve) 60 and the driver 40. It is rotationally constrained to the dose indicator 60 via a splined interface. It moves along a helical path relative to the driver 40, via a threaded interface 44, when relative rotation occurs between the dose indicator 60 and driver 40 during dialling. This is shown in FIG. 13. As an alternative, the nut 50 may be splined to the driver 40 and threaded to the dose indicator 60. In the embodiment shown in the Figures, the nut 50 is a full nut, but in alternative embodiments it may be a half nut, i.e. a component extending approximately 180° around the center axis of the device. As a further alternative, if the driver 40 was formed from two separate components that became rigidly engaged during assembly then the nut 50 could also be a complete nut.

Figure 8:
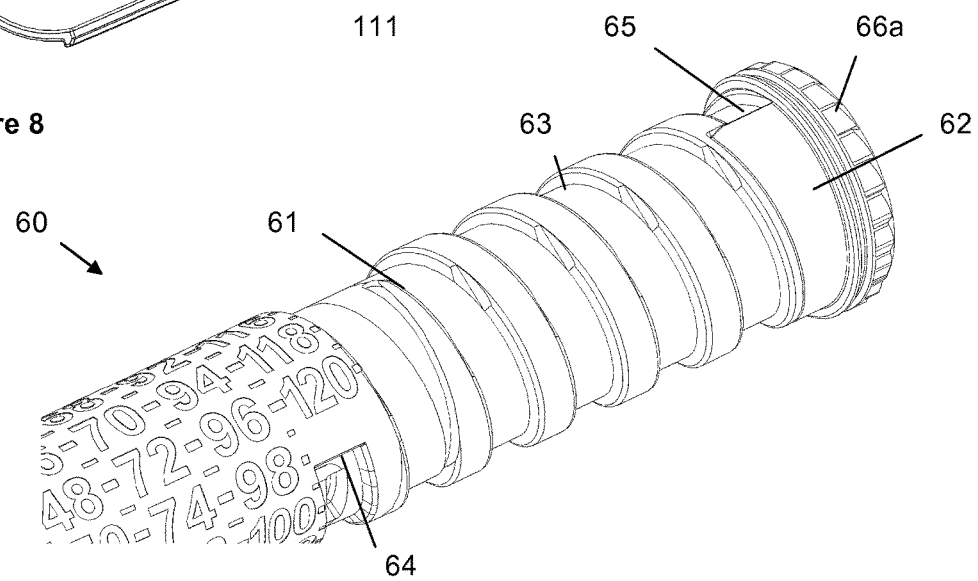
FIG. 8 shows a perspective view of the dose indicator of the device of FIG. 1.
Figure 9:
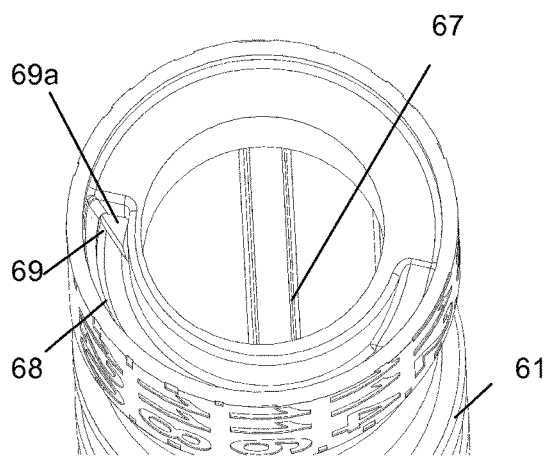
FIG. 9 shows an enlarged detail of the dose indicator of FIG. 8.
Figure 9A:
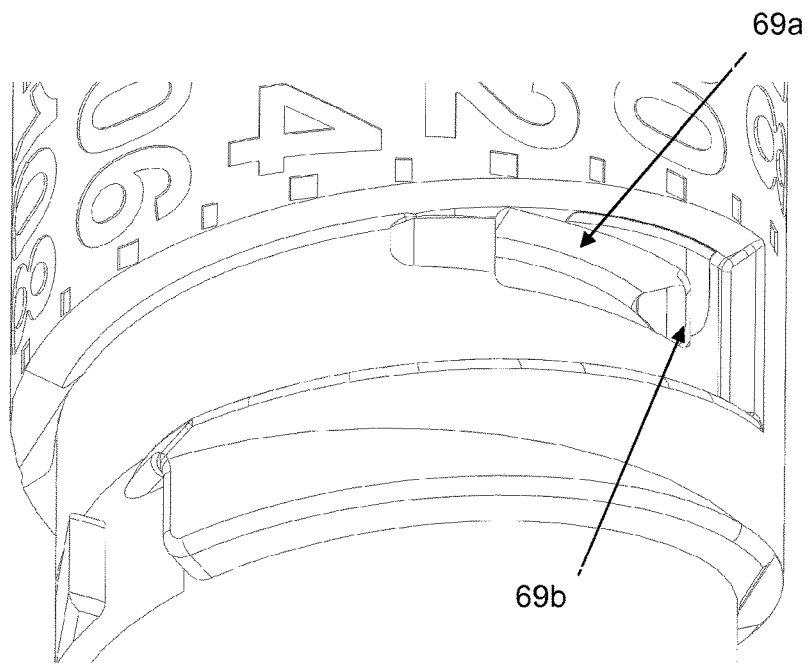
FIG. 9*a* shows an enlarged detail of FIG. 9.
Figure 9B:
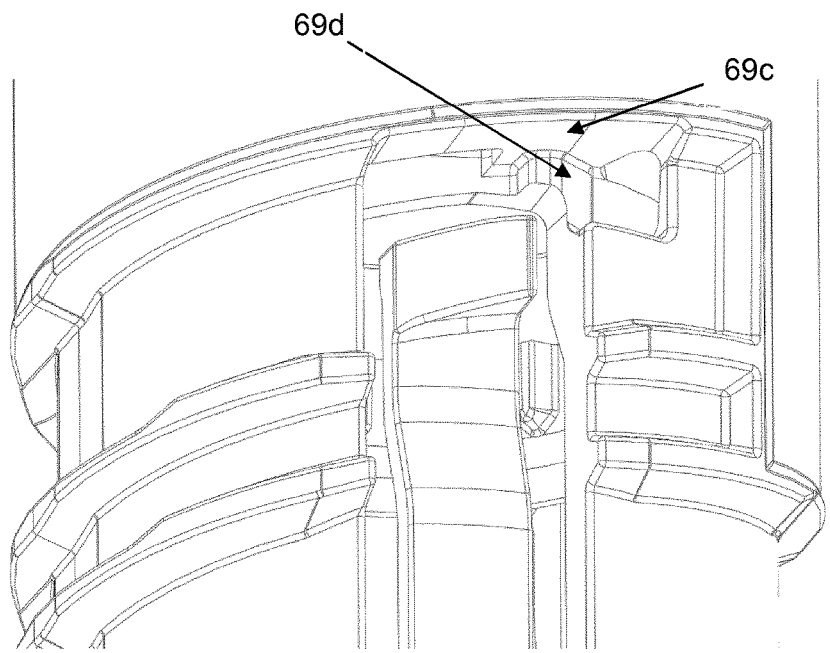
FIG. 9*b* shows an alternative enlarged detail of FIG. 9.
Figure 14:
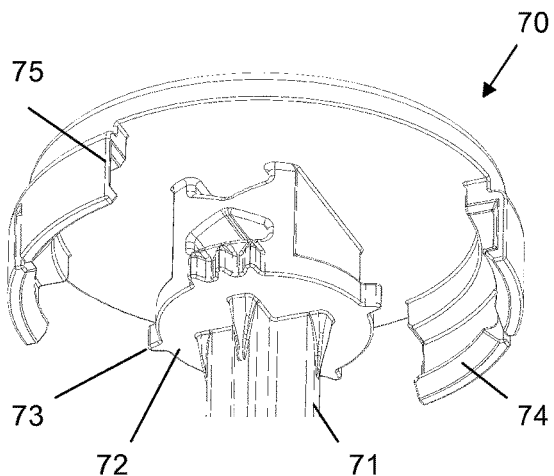
FIG. 14 shows an enlarged detail of the button of the device of FIG. 1.
Figure 15:
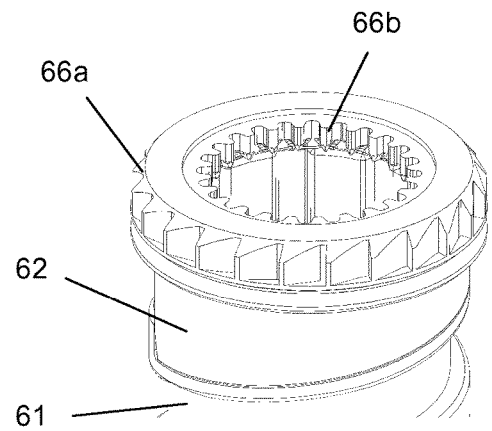
FIG. 15 shows an enlarged detail of the dose indicator of the device of FIG. 1.
Figure 18:
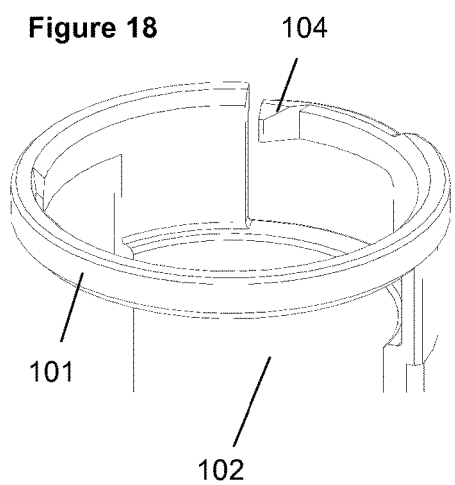
FIG. 18 shows an enlarged detail of the locking element of the device of FIG. 1.
Figure 19:
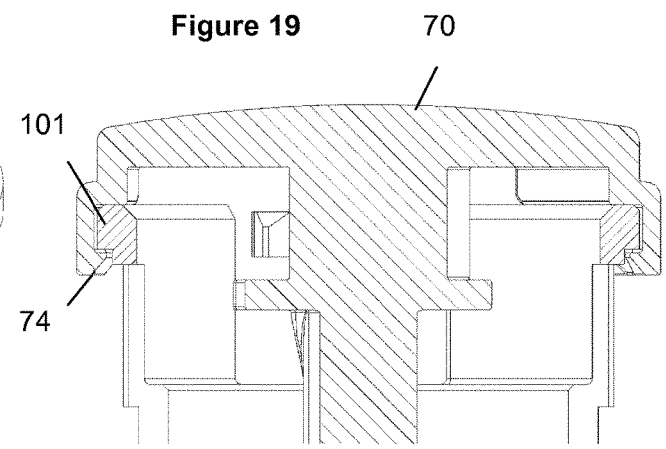
FIG. 19 shows an enlarged detail of the locking element and button of the device of FIG. 1.

The dose indicator (number sleeve) 60 is a tubular element as shown in FIGS. 8 and 9. In the embodiment depicted in the Figures the dose indicator is a sub assembly comprising a number sleeve lower 61 and a number sleeve upper 62 which are rigidly fixed to each other during assembly to form the dose indicator. The number sleeve lower and the number sleeve upper are separate components only to simplify mould tooling and assembly. However, they could be integrated into a single component part. This sub assembly is constrained to the housing 10 by features towards the proximal end to allow rotation but not translation. The number sleeve lower is marked with a sequence of numbers, which are visible through the gauge element 110 and the window (slot 11) through the housing 10, to denote the dialled dose of medicament. Further, the number sleeve lower 61 has a portion with an outer thread 63 engaging the gauge element 110. End stops 64, 65 are provided at the opposite ends of thread 63 to limit relative movement with respect to the gauge element 110. Clicker features 66a are provided on number sleeve upper 62 for engaging a corresponding clicker feature of the locking element 100 during dose dispensing (FIG. 15 and FIG. 18). Clutch features 66b are provided inwardly directed on number sleeve upper 62 for engagement with splines 73 of the button 70 during dose setting and dose correction (FIG. 14 and FIG. 15). A further clicker feature 66c interacts with clicker arm 105. In addition, the number sleeve lower 61 is rotationally constrained to the nut 50 and to the clutch plate 120 via a splined interface comprising at least one longitudinal spline 67 (FIG. 9). An interface for attachment of the torsion spring 90 to the number sleeve lower 61 comprises large lead-ins and a groove feature 68 with a pocket (anchor point 69a, 69c) for receiving a first coil or hook portion of the spring. The groove 68 has an end feature in the form of a ramp 69b, 69d that is in interference with the hook portion 91 of the spring. An inner flange is shown in FIG. 9 for reinforcing the area of the dose indicator connected to the torsion spring 90. The design of the groove 68 is such that the spring 90 may be received within the pocket without interfering with the gauge element 110. Two embodiments of an anchor point 69a and 69c and an end feature 69b and 69d in the form of a ramp are shown in FIGS. 9a and 9b.

The button 70 forms the proximal end of the device. The button is permanently splined to the dose selector 80 and splined to the number sleeve upper 62 when the button is not pressed. This spline interface is disconnected when the button 70 is pressed. A central stem 71 extends distally from the proximal actuation face of the button 70. The stem 71 is provided with a flange 72 carrying splines 73 for engagement with splines 66b of the number sleeve upper 62 (FIG. 14 and FIG. 15). The button 70 has a discontinuous annular skirt forming two clips 74 for axially constraining the button to a bead or flange of the locking element 100. Further spline features for engagement with the dose selector 80 are provided by the radially extending surfaces on the sides of the clips 74. A slit 75 is provided for making the clips more flexible.

The dose selector 80 or dose dial grip is a sleeve-like component with a serrated outer skirt. The dose selector 80 is axially constrained to the housing 10. It is rotationally constrained, via a splined interface, to the dose button 70. This splined interface which includes grooves 81 interacting with the spline features remains engaged irrespective of the dose button 70 axial positions.

Figure 10:
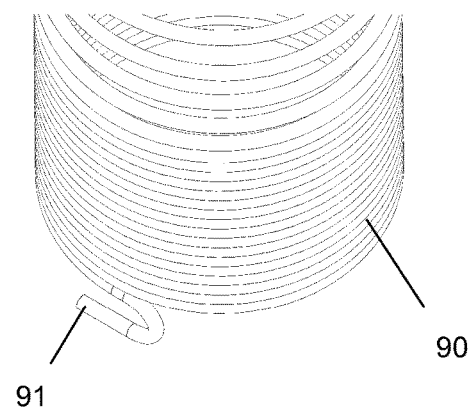
FIG. 10 shows a perspective view of the torsion spring of the device of FIG. 1.

The torsion spring 90 is attached with its distal end to the housing 10 and with its other end to the number sleeve lower 61. The torsion spring 90 is pre-wound upon assembly, such that it applies a torque to the dose indicator 60 when the mechanism is at zero units dialled. The action of rotating the dose selector 80, to set a dose, rotates the dose indicator 60 relative to the housing 10, and charges the torsion spring 90 further. The torsion spring 90 is located inside the dose indicator 60 and surrounds a distal portion of the driver 40. As shown in FIG. 10, the spring has a hook 91 at one end for attachment on the dose indicator 60. A similar hook end may be provided at the opposite end for attachment on the housing.

Figure 20:
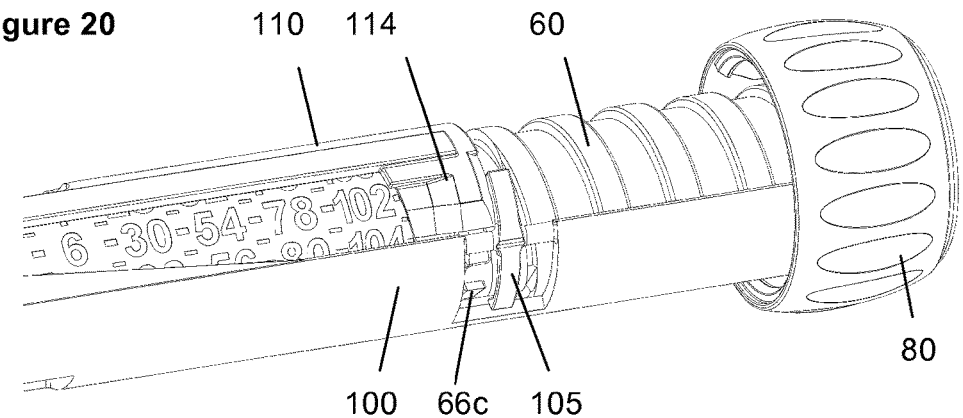
FIG. 20 shows a partially cut away view of the device of FIG. 1.

The locking element 100 is rotationally fixed to the housing 10 but allowed to translate axially. Axial movement is effected and controlled by the dose button 70 which is axially clipped onto the locking element 100 (FIG. 18). The locking element 100 comprises a proximal ring portion 101 and an arm portion 102 extending distally from the ring portion. Near its distal end, the arm portion 102 has teeth 103 for releasably coupling the tooth interface 41 of driver 40 to the housing 10 via the locking element 100 (FIG. 11). Further, a compliant cantilever clicker arm 104 is arranged within the ring portion 101 to produce a tactile feedback due to an engagement with splines 66a on the number sleeve upper 62 when the locking element is in its dose dispensing position. An additional clicker arm 105 is pivotally arranged on a torsion beam and interacts with clicker features on the dose indicator 60 at the end of dose dispensing (FIG. 20).

Figure 7:
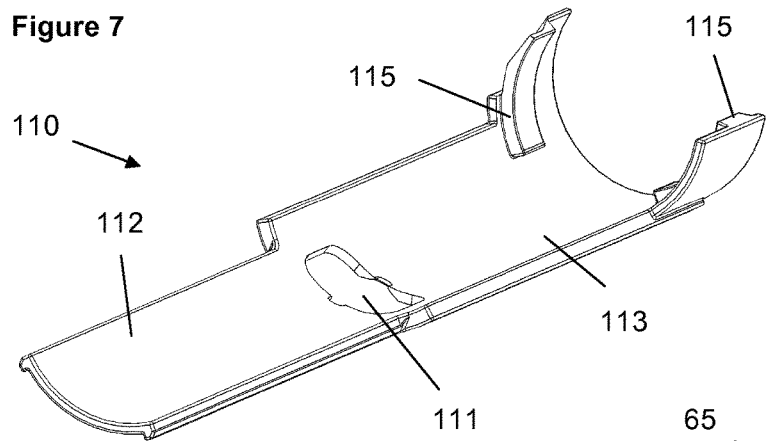
FIG. 7 shows a perspective view of the gauge element of the device of FIG. 1.

The gauge element 110 is a window element which is constrained to prevent rotation but allow translation relative to the housing 10 via a splined interface. It is also in threaded engagement to the dose indicator 60 such that rotation of the dose indicator 60 causes axial translation of the gauge element 110. The gauge element 110 is positioned in housing 10 such that it is guided within slot 11 and closes same. As shown in FIG. 7, it is a generally plate or band like component having a central aperture 111 or window and two flanges 112, 113 extending on either side of the aperture. The flanges 112, 113 are preferably not transparent and thus shield or cover the dose indicator 60, whereas the aperture 111 or window allows viewing a portion of the number sleeve lower 61. Further, gauge element 110 has a ramp 114 interacting with a clicker arm 105 of the locking element 100 at the end of dose dispensing (FIG. 20). The gauge element 110 has helical features 115 on its inner surface which engage with the helical thread cut in the number sleeve lower 61 such that rotation of the dose indicator 60 causes axial translation of the gauge element. These helical features 115 on the gauge element 110 also create stop abutments against the end of the helical cut in the dose indicator 60 to limit the minimum and maximum dose that can be set.

The clutch plate 120 is a ring-like component (FIG. 12) arranged on the proximal end of the driver 40 near flange 42. It is surrounded by the dose indicator 60 and splined thereto by spline 67. It is also coupled to the driver 40 via a ratchet interface 43, 121, which occurs on an axial abutment. The ratchet 43, 121 provides a detented position between the dose indicator 60 and driver 40 corresponding to each dose unit, and engages different ramped tooth angles during clockwise and anti-clockwise relative rotation. FIG. 12 shows the clutch plate 120 together with the proximal end of the device in more detail.

The clutch spring 130 is a compression spring located interposed between flange 72 of button 70 and clutch plate 120. It acts on the clutch plate 120 allowing the ratchet teeth 43, 121 to bump over each other during dose setting against the axial force of the spring. The axial position of the locking element 100, clutch plate 120 and button 70 is defined by the action of the clutch spring 130, which applies a force on the button 70 in the proximal direction. This force is reacted by the clutch plate, via the driver 40, to the housing 10 and ensures that the ratchet interface is always engaged. In the "at rest" position, this ensures that the button splines are engaged with the number sleeve upper 62, and the teeth 41 of driver 40 are engaged with the locking element 100 and that the ratchet interface is engaged.

The bearing 140 is axially constrained to the lead screw 30 (FIG. 16) and acts on the bung within the liquid medicament cartridge 150. It is axially clipped to the lead screw 30, but free to rotate. The bearing 140 comprises a disc 141 having a stem 142 extending in the proximal direction. The stem 142 has at its proximal end a convex contact surface 143. In addition, a recessed portion 144 is provided on the stem 142. The curvature of the convex contact surface 143 and the concave contact surface 34 is chosen such that the contact diameter between the bearing 140 and lead screw 30 is small to minimize the frictional losses at this interface. The design of the clip interface between bearing 140 and lead screw 30 permits the lead screw 30 to be assembled axially, from the proximal end and through the thread engagement to the housing 10, which simplifies assembly. In addition, this design allows a simple "open and shut" mould tooling for both components. This can be achieved by ensuring that none of the surface of a part is hidden when viewed from either of the two opposing sides of the part. For example, all faces of the lead screw 30 are completely visible from either one side of a longitudinal plane or the other side of the same plane.

The cartridge 150 is received in cartridge holder 20 (FIG. 4). The cartridge 150 may be a glass ampoule having a moveable rubber bung 151 at its proximal end. The distal end of cartridge 150 is provided with a pierceable rubber seal which is held in place by a crimped annular metal band. In the embodiment depicted in the Figures, the cartridge 150 is a standard 1.5 ml cartridge. The device is designed to be disposable in that the cartridge 150 cannot be replaced by the user or health care professional. However, a reusable variant of the device could be provided by making the cartridge holder 20 removable and allowing backwinding of the lead screw 30 and the resetting of nut 50.

With the device in the 'at rest' condition (e.g. FIGS. 2, 4 and 5), the dose indicator 60 is positioned against its zero dose abutment with the gauge element 110 and the button 70 is not depressed. Dose marking '0' on the dose indicator 60 is visible through the window 11 of the housing 10 and gauge element 110. The Torsion Spring, which has a number of pre-wound turns applied to it during assembly of the device, applies a torque to the dose indicator 60 and is prevented from rotating by the zero dose abutment 64 between dose indicator 60 and gauge element 110.

The automated assembly of the torsion spring 90 into the dose indicator 60 (FIGS. 9 and 9*a*) can be achieved by incorporating large lead-ins and the groove feature 68 to the dose indicator 60. As the torsion spring 90 is rotated during assembly, the hook end form locates in the groove feature 68 before engaging the anchor point 69*a* in the dose indicator 60. To help to prevent the torsion spring 90 disengaging the anchor point during subsequent assembly steps it is possible to create an interference. This interference occurs between the outer surface of the hook end and the outer surface of the groove in the dose indicator 60. In an alternative embodiment (FIG. 9*b*), it occurs between the inner surface of the hook end and the outer surface of the anchor point 69*c* in the dose indicator 60.

The user selects a variable dose of liquid medicament by rotating the dose selector 80 clockwise, which generates an identical rotation in the dose indicator 60. Rotation of the dose indicator 60 causes charging of the torsion spring 90, increasing the energy stored within it. As the dose indicator 60 rotates, the gauge element 110 translates axially due to its threaded engagement with the number sleeve lower 61 thereby showing the value of the dialled dose (FIG. 7). The gauge element 110 has flanges 112, 113 either side of the window area 111 which cover the numbers printed on the dose indicator 60 adjacent to the dialled dose to ensure only the set dose number is made visible to the user.

Figure 3:
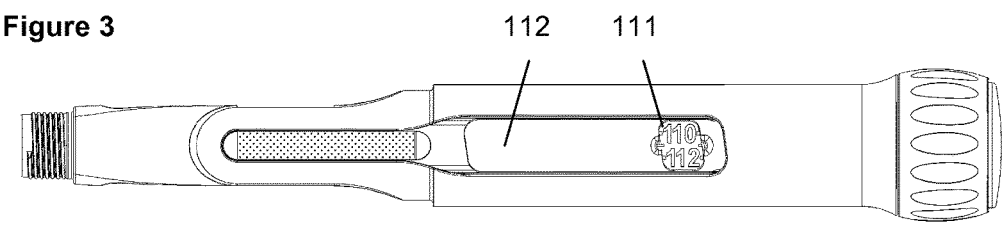
FIG. 3 shows a top view of the device of FIG. 1 with a dose of 111 units set.

One specific element of this mechanism is inclusion of a visual feedback feature in addition to the discrete dose number display typical on devices of this type. The distal end of the gauge element 110 creates a sliding scale (although this could be formed using a separate component engaged with the dose indicator 60 on a different helical track if desired) through the small window 11 in the housing 10. As a dose is set, by the user, the gauge element 110 translates axially, the distance moved proportional to the magnitude of the dose set. FIGS. 2 and 3 show the device with a dose of zero set (FIG. 2) and a dose of 111 units set (FIG. 3). A comparison of FIGS. 2 and 3 reveals that window area 111 moves from the distal side to the proximal side as an increasing dose is set. This feature gives clear feedback to the user regarding the approximate size of the dose set. The dispense speed of an auto-injector mechanism may be higher than for a manual injector device, so it may not be possible to read the numerical dose display during dispense. The gauge feature provides feedback to the user during dispense regarding dispense progress without the need to read the dose number itself.

The gauge display may be formed by an opaque sliding element revealing a contrasting coloured component underneath. Alternatively, the revealable component may be printed with coarse dose numbers or other indices to provide more precise resolution. In addition, the gauge display simulates a syringe action during dose set and dispense.

The mechanism utilizes a dose selector 80 with an increased diameter relative to the housing 10 which aids dialling although this is not a requirement of the mechanism. This feature is particularly useful (but not essential) for an auto-injector mechanism where a power supply is charged during dose setting and the torque required to turn the dose selector 80 may be higher than for a non-auto injector device.

The driver 40 is prevented from rotating as the dose is set and the dose indicator 60 rotated, due to the engagement of its splined teeth 41 with the locking element 100 (FIG. 11). Relative rotation must therefore occur between the clutch plate 120 and driver 40 via the ratchet interface (FIG. 12).

The user torque required to rotate the dose selector 80 is a sum of the torque required to wind up the torsion spring 90, and the torque required to overhaul the ratchet feature 43, 121. The clutch spring 130 is designed to provide an axial force to the ratchet feature and to bias the clutch plate 120 onto the driver 40. This axial load acts to maintain the ratchet teeth engagement of the clutch plate 120 and driver 40.

As the user rotates the dose selector 80 sufficiently to increment the mechanism by 1 increment, the dose indicator 60 rotates relative to the driver 40 by 1 ratchet tooth 43, 121. At this point the ratchet teeth re-engage into the next detented position. An audible click is generated by the ratchet re-engagement, and tactile feedback is given by the change in torque input required.

Relative rotation of the dose indicator 60 and the driver 40 also causes the last dose nut 50 with stop 51 to travel along its threaded path 44, towards its last dose abutment stop 46 on the driver 40 (FIG. 13).

With no user torque applied to the dose selector 80, the dose indicator 60 is now prevented from rotating back under the torque applied by the torsion spring 90, solely by the ratchet engagement between the clutch plate 120 and the driver 40. The torque necessary to overhaul the ratchet 43, 121 in the anti-clockwise direction is a function of the axial load applied by the clutch spring 130, the anti-clockwise ramp angle of the ratchet, the friction coefficient between the mating surfaces and the mean radius of the ratchet features 43, 121. The torque necessary to overhaul the ratchet 43, 121 must be greater than the torque applied to the dose indicator 60 (and hence clutch plate 120) by the torsion spring 90. The ratchet ramp angle is therefore increased in the anti-clockwise direction to ensure this is the case whilst ensuring the dial-up torque is as low as possible.

The user may now choose to increase the selected dose by continuing to rotate the dose selector 80 in the clockwise direction. The process of overhauling the ratchet interfaces 43, 121 between the dose indicator 60 and driver 40 is repeated for each dose increment. Additional energy is stored within the torsion spring 90 for each dose increment and audible and tactile feedback is provided for each increment dialled by the re-engagement of the ratchet teeth 43, 121. The torque required to rotate the dose selector 80 increases as the torque required to wind up the torsion spring 90 increases. The torque required to overhaul the ratchet in the anti-clockwise direction must therefore be greater than the torque applied to the dose indicator 60 by the torsion spring 90 when the maximum dose has been reached.

If the user continues to increase the selected dose until the maximum dose limit is reached, the dose indicator 60 engages with its maximum dose abutment 65 (FIG. 8) on the gauge element 110. This prevents further rotation of the dose indicator 60, clutch plate 120 and dose selector 80.

Depending on how many increments have already been delivered by the mechanism, during selection of a dose, the last dose stop 51 on the last dose nut 50 may contact the last dose stop 46 on the driver 40 (FIG. 13). The abutment prevents further relative rotation between the dose indicator 60 and the driver 40, and therefore limits the dose that can be selected. The position of the last dose nut 50 is determined by the total number of relative rotations between the dose indicator 60 and driver 40, which have occurred each time the user sets a dose.

With the mechanism in a state in which a dose has been selected, the user is able to deselect any number of increments from this dose. Deselecting a dose is achieved by the user rotating the dose selector 80 anti-clockwise. The torque applied to the dose selector 80 by the user is sufficient, when combined with the torque applied by the torsion spring 90, to overhaul the ratchet 43, 121 between the clutch plate 120 and driver 40 in the anti-clockwise direction (FIG. 12). When the ratchet is overhauled, anti-clockwise rotation occurs in the dose indicator 60 (via the clutch plate 120), which returns the dose indicator 60 towards the zero dose position, and unwinds the torsion spring 90. The relative rotation between the dose indicator 60 and driver 40 causes the last dose nut 50 to return along its helical path, away from the last dose stop 46 (FIG. 13).

With the mechanism in a state in which a dose has been selected, the user is able to activate the mechanism to commence delivery of a dose. Delivery of a dose is initiated by the user depressing the button 70 axially. FIG. 6 shows the device with button 70 pressed.

When the button 70 is depressed, splines 66b, 73 between the button 70 and dose indicator 60 are disengaged (FIG. 14 and FIG. 15), rotationally disconnecting the button 70 and dose selector 80 from the delivery mechanism (so that the dose selector 80 does not rotate during dispense). The button 70 acts on the locking element 100, which travels axially and disconnects the splined engagement 41, 103 with the driver 40 (FIG. 11). The driver 40 can now rotate and is driven by the torsion spring 90 via the dose indicator 60, and clutch plate 120. Rotation of the driver 40 causes the lead screw 30 to rotate due to their splined engagement, and the lead screw 30 then advances due to its threaded engagement to the housing 10. The dose indicator 60 rotation also causes the gauge element 110 to traverse axially back to its zero position whereby the zero dose abutment 64 stops the mechanism (FIG. 10).

The bearing 140 is axially clipped to the lead screw 30, but free to rotate. Since the bearing is in direct contact with the bung 151, it does not rotate as the lead screw 30 rotates and advances during dose dispense.

Tactile feedback during dose dispense is provided via a compliant cantilever clicker arm 104 integrated into the proximal ring portion 101 of the locking element 100 (FIG.

18). This interfaces radially with ratchet features on the outer surface of the proximal end of the dose indicator 60 (FIG. 15), whereby the ratchet tooth spacing corresponds to the dose indicator 60 rotation required for a single increment dispense. During dispense, as the dose indicator 60 rotates and the locking element 100 is rotationally coupled to the housing 10, the ratchet features engage with the clicker arm 104 to produce an audible click with each dose increment delivered.

Delivery of a dose continues via the mechanical interactions described above while the user continues to depress the button 70. If the user releases the button 70, the clutch spring 130 returns the button 70 to its 'At Rest' position, withdrawing the locking element 100 through the axial constraint between these two components, engaging the splines 41, 103 to the driver 40, preventing further rotation and stopping dose delivery (FIG. 11).

During delivery of a dose, the driver 40 and dose indicator 60 rotate together, so that no relative motion in the last dose nut 50 occurs. The last dose nut 50 therefore travels axially on the driver 40 during dialling only.

Once the delivery of a dose is stopped, by the dose indicator 60 returning to the zero dose abutment 64, the user may release the button 70, which will re-engage the locking element 100 spline teeth 41, 103 with the driver 40. The mechanism is now returned to the 'At Rest' condition.

It is possible to angle the spline teeth 41, 103 on either the driver 40 or locking element 100 so that when the button 70 is released the re-engagement of the spline teeth fractionally 'backwinds' the driver 40 thereby removing the engagement of the dose indicator 60 to the gauge element 110 zero dose stop abutment. This compensates for the effect of clearances in the mechanism (for example due to tolerances) which could otherwise lead to slight advancement of the lead screw 30 and medicament dispense when the device is dialled for the subsequent dose (due to the dose indicator 60 zero dose stop no longer restraining the mechanism and instead the restraint returning to the splines between the driver 40 and locking element 100).

Figure 21A:
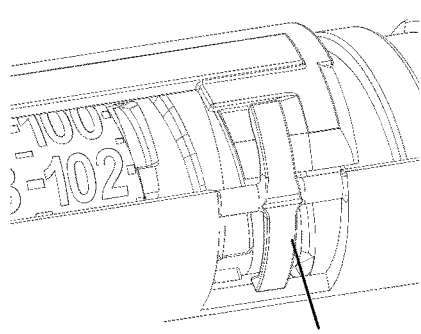
FIGS. 21 *a-f* show in enlarged views the sequence of generating a click at the end of dose dispensing.

At the end of dose, additional audible feedback is provided in the form of a "click", distinct from the "clicks" provided during dispense, to inform the user that the device has returned to its zero position via the interaction of three components, the dose indicator 60, gauge element 110 and locking element 100. This embodiment allows feedback to only be created at the end of dose delivery and not created if the device is dialled back to, or away from, the zero position. FIGS. 20 and 21a show the position of the features when the device is in the dose set condition. It can be seen that the gauge element 110 does not contact the clicker arm 105 of the locking element 100 when the device is in the "at rest" condition, i.e. 0 units dialled and the button 70 not pressed. Therefore, during storage the clicker arm 105 is not deflected (and will not suffer creep deformation).

During dose delivery, the locking element 100 is translated axially, whereby the clicker arm 105 on the locking element 100 axially aligns with the clicker feature 66c on the dose indicator 60. As the gauge element 110 returns axially to the zero unit position, the ramp feature 114 contacts the clicker arm 105. This causes the clicker arm 105 to rock (through twisting of the torsion beam) and, as the end contacting the gauge element 110 is deflected radially outward, the opposite end is deflected radially inwards to force the clicker arm tooth into engagement with the dose indicator 60 clicker feature 66c.

Figure 21C:
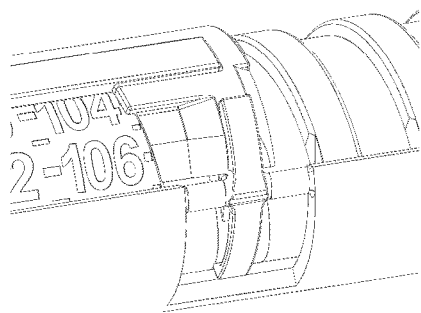
Figure 21E:
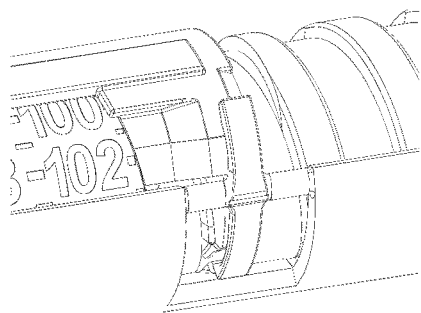
Figure 21B:
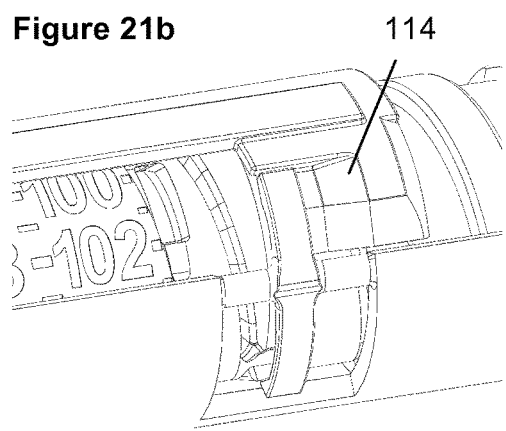
Figure 21D:
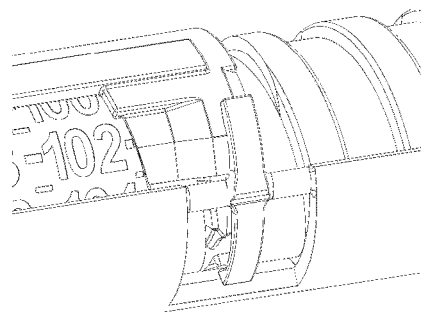
Figure 21F:
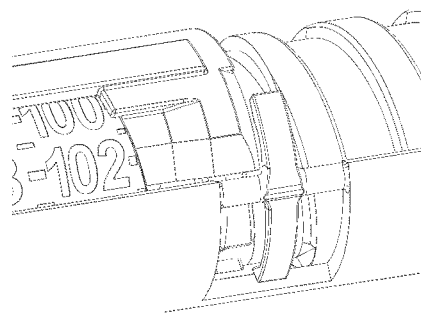

FIGS. 21a to 21f show the component interactions. In FIG. 21a a dose is dialled with approximately one full dial turn applied to the number sleeve (dose indicator 60). The gauge element 110 is translated in the proximal direction away from the zero unit position. Clicker arm 105 of the locking element 100 is not deflected. In FIG. 21b dose dispensing starts as the button 70 is depressed which translates locking element 100 axially, whereby the clicker arm 105 on the locking element 100 axially aligns with the protrusion on the dose indicator 60. At this time, the clicker arm 105 is still not deflected. FIG. 21c shows the end of dispensing with only 4 units remaining to be dispensed. As the gauge element 110 returns axially to the zero unit position, the ramp 114 contacts the clicker arm 105. This causes the clicker arm 105 to rock (around the torsion beam) and, as the end contacting the gauge element 110 is deflected radially outward, the opposite end is deflected radially inwards. In FIG. 21d dispensing continues with only 0.5 units remaining. As the clicker feature on dose indicator 60 rotates past the tooth on clicker arm 105, the clicker arm is "charged" and deflected radially outwards. In FIG. 21e the dose is fully dispensed. As clicker ramp on dose indicator 60 continues to rotate, the tooth on the clicker arm 105 drops off the sharp edge of the clicker feature on the dose indicator 60 and creates a distinct "click". In FIG. 21f button 70 is released which allows the clutch spring 130 to return the button 70 and the locking element 100 to their "at rest" axial positions. This also allows the clicker arm 105 to rock back to its original position as the torsion beam relaxes. This arrangement prevents any of these features remaining stressed for significant periods of time, minimising the risk of creep deformation.

Figure 16:
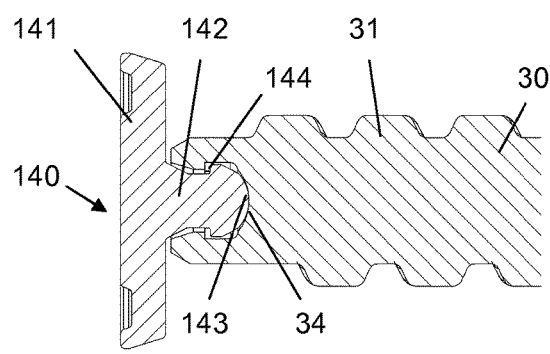
FIG. 16 shows an enlarged detail of the lead screw and bearing of the device of FIG. 1.
Figure 17:
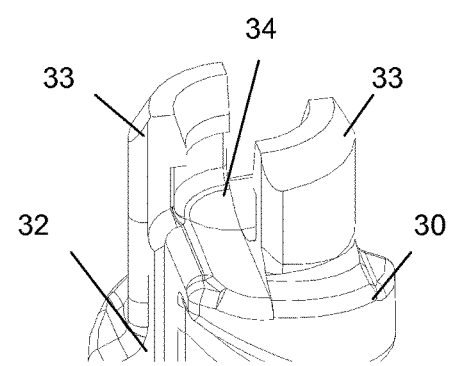
FIG. 17 shows an enlarged detail of the lead screw of the device of FIG. 1.
Figure 22:
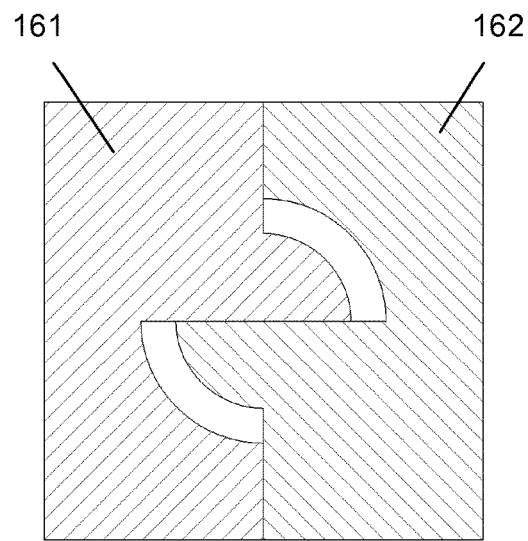
FIG. 22 shows a sectional view of a tool for moulding the lead screw of FIG. 17.

A tool for moulding the lead screw 30 as shown in FIGS. 16 and 17 is schematically depicted in FIG. 22. This tool comprises only two tool parts 161, 162 that slide relative to each other along the same axis, namely parallel to the plane of FIG. 22. The tool parts 161, 162 are shaped such that during opening the tool does not interfere with the moulded part, i.e. the clip arms 33. Although not shown in FIG. 22, tool parts 161, 162 vary in shape along the longitudinal axis of the lead screw 30 (piston rod). For example, the cavity defined by the two tool parts 161, 162 has a roughly circular cross section in the threaded region of the rod.

Figure 23:
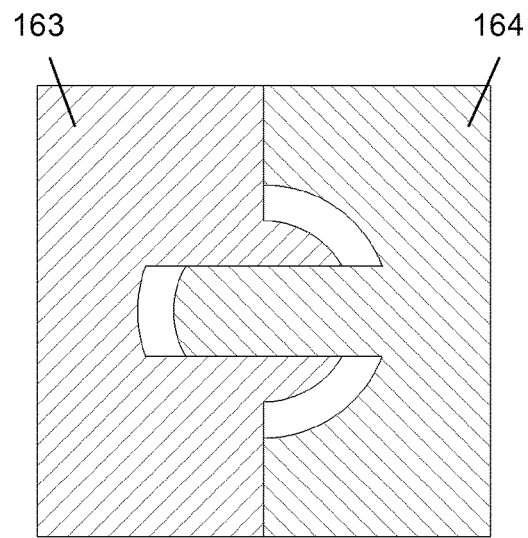
FIG. 23 shows a sectional view of a tool for moulding an alternative lead screw.
Figure 24:
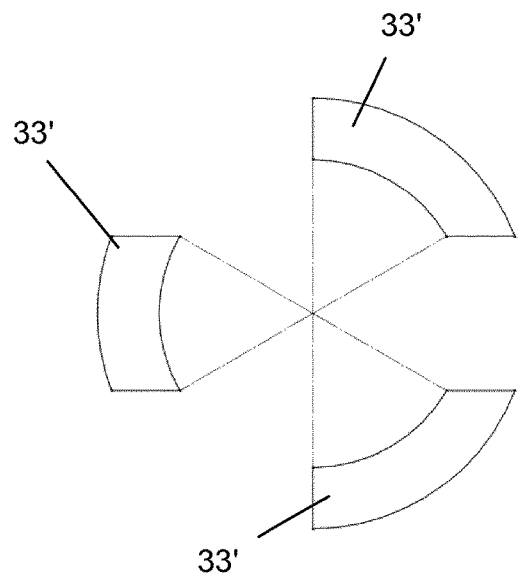
FIG. 24 shows a sectional view of a lead screw moulded with the tool of FIG. 23.

An alternative design of the clip arms 33' of lead screw 30 and a tool for moulding same is shown in FIGS. 23 and 24. Again, the tool comprises only two tool parts 163, 164 that slide relative to each other along the same axis, namely parallel to the plane of FIG. 23. However, the tool parts 163, 164 are shaped such that three clip arms 33' are formed on the distal end of lead screw 30. Similar as with the lead screw 30 of FIGS. 16 and 17, the internal faces of the clip arms 33' on the threaded rod 30 subtend a total angle of roughly 180° about the longitudinal axis. This allows simple open and shut moulding of the rod and its clip features, while the clip arms 33, 33' are suitable for engaging retaining stem 142.

REFERENCE NUMERALS 10 housing
11 slot
12 flange-like inner wall
20 cartridge holder
30 lead screw (piston rod)
31 outer thread
32 longitudinal groove (track)
33, 33' clip arm (retaining clip)
34 concave contact surface
40 driver 41 splined tooth interface
42 teeth
43 flange (with teeth)
44 threaded section
45 spline
46 last dose stop
50 nut
51 last dose stop
60 dose indicator (number sleeve)
61 number sleeve lower
62 number sleeve upper
63 outer thread
64, 65 end stop
66a clicker feature (spline)
66b clutch feature (spline)
66c clicker feature
67 spline
68 groove
69 ramp
69a anchor point
69b end feature
69c anchor point
69d end feature
70 button
71 stem
72 flange
73 spline
74 clip
75 slit
80 dose selector
81 groove
90 torsion spring
91 hook
100 locking arm
101 proximal ring portion
102 arm portion
103 teeth
104, 105 clicker arm
110 gauge element
111 aperture
112, 113 flange
114 ramp
120 clutch plate
121 ratchet interface
130 clutch spring
140 bearing
141 disc
142 (retaining) stem
143 convex contact surface
144 recessed portion
150 cartridge
151 bung
161-164 tool part

The invention claimed is:

1. A drug delivery device for selecting and dispensing a number of user variable doses of a medicament, the drug delivery device comprising: a housing defining a longitudinal axis and having a tubular portion with an inner thread, a piston rod having a threaded portion and a distal end, and a bearing having a distal face and a proximal face, wherein the bearing comprises a retaining stem protruding from the proximal face, wherein the piston rod comprises a distal portion having an outer diameter which is smaller than an inner diameter of the inner thread of the tubular portion, and, a retaining clip engaging the retaining stem at a distal end of the piston rod, and wherein an axial length of the tubular portion is smaller than or equal to an axial distance between the proximal face of the bearing and the distal end of the threaded portion of the piston rod.

2. The drug delivery device according to claim 1, wherein the tubular portion extends between its distal end and a proximal side of the inner thread.

3. The drug delivery device according to claim 1, wherein the distal portion of the piston rod has a cylindrical outer surface.

4. The drug delivery device according to claim 1, wherein the retaining clip comprises a distally extending clip arm located at the distal end of the piston rod defining an insertion space for receiving the retaining stem.

5. The drug delivery device according to claim 1, wherein internal faces of the retaining clip subtend a total angle between 150° and 190° about the longitudinal axis of the piston rod.

6. The drug delivery device according to claim 1, wherein a first convex contact surface is provided on one of the retaining stem and the retaining clip and a second contact surface is provided on the other of the retaining stem and the retaining clip, and wherein a radius of curvature of the first convex contact surface is smaller than a radius of curvature of the second contact surface.

7. The drug delivery device according to claim 1, further comprising
a dose setting member rotatable relative to the housing during dose setting,
a drive member rotationally constrained to the piston rod and rotationally constrained to the housing in a first dose setting mode and rotatable relative to the housing in a second dose dispensing mode,
an actuation button movable relative to the housing in a direction parallel to the longitudinal axis between a first dose setting position and a second dose dispensing position for switching the drug delivery device between the first dose setting mode and the second dose dispensing mode, and
a ratchet for transmitting torque from the dose setting member to the drive member during dose dispensing and allowing relative rotational movement between the dose setting member and the drive member during dose setting, the ratchet comprising first ratchet features rotationally constrained to the drive member and second ratchet features rotationally constrained to the dose setting member.

8. The drug delivery device according to claim 7, wherein the first ratchet features and the second ratchet features comprise teeth having a ramp angles allowing to overhaul the ratchet for dose correction.

9. The drug delivery device according to claim 7, wherein the housing has a first aperture or window, and the drug delivery device further comprises
a dose indicator positioned within the housing and rotatable with respect to the housing during dose setting and during dose dispensing,
a gauge element interposed between the housing and the dose indicator, wherein the gauge element has a second aperture or window positioned with respect to the first aperture or window of the housing such that at least a part of the dose indicator is visible through the first and second apertures or windows, and wherein the gauge element is axially guided within the housing and in threaded engagement with the dose indicator such that rotation of the dose indicator causes an axial displacement of the gauge element, and
a resilient member adapted to provide a force necessary for ejecting a dose from the drug delivery device.

10. The drug delivery device according to claim 9, wherein the resilient member is a torsion spring which is strained during dose setting.

11. The drug delivery device according to claim 9, further comprising a second clutch configured to rotationally couple the actuation button to the dose indicator when the actuation button is in the first dose setting position and configured to de-couple the actuation button from the dose indicator when the actuation button is in the second dose dispensing position.

12. The drug delivery device according to claim 1, comprising a limiter mechanism defining a maximum settable dose and a minimum settable dose and/or a last dose protection mechanism for preventing the setting of a dose exceeding an amount of liquid left in a cartridge.

13. The drug delivery device according to claim 1, further comprising a cartridge containing a medicament.

\* \* \* \* \*